(12) United States Patent
Russo

(10) Patent No.: US 8,096,300 B2
(45) Date of Patent: Jan. 17, 2012

(54) ENDOTRACHEAL TUBE HOLDER

(75) Inventor: Ronald D. Russo, Barrington, RI (US)

(73) Assignee: Dale Medical Products, Inc., Plainville, MA (US)

( * ) Notice: Subject to any disclaimer, the term of this patent is extended or adjusted under 35 U.S.C. 154(b) by 1374 days.

(21) Appl. No.: 11/295,407

(22) Filed: Dec. 5, 2005

(65) Prior Publication Data

US 2006/0118120 A1    Jun. 8, 2006

Related U.S. Application Data

(60) Provisional application No. 60/632,806, filed on Dec. 3, 2004.

(51) Int. Cl.
*A62B 9/04* (2006.01)
*A61M 16/00* (2006.01)

(52) U.S. Cl. ......... 128/207.17; 128/202.27; 128/207.14; 604/179; 604/180

(58) Field of Classification Search ............ 604/180, 604/179; 128/877, 206.25, 207.17, 207.14, 128/202.27, 912, DIG. 26
See application file for complete search history.

(56) References Cited

U.S. PATENT DOCUMENTS

| | | |
|---|---|---|
| 1,443,820 A | 1/1923 | Hudson |
| 1,445,010 A | 2/1923 | Feinberg |
| 1,592,345 A | 7/1926 | Drager |
| 2,191,782 A | 2/1940 | Valane |
| 2,693,182 A | 11/1954 | Phillips |
| 2,756,742 A | 7/1956 | Barton |
| 2,820,457 A | 1/1958 | Phillips |
| 2,857,911 A | 10/1958 | Bennett |
| 2,908,269 A | 10/1959 | Aiming Cheng |
| 3,602,227 A | 8/1971 | Andrew |
| 3,658,058 A | 4/1972 | Neidhart et al. |

(Continued)

FOREIGN PATENT DOCUMENTS

DE    101 15 881 A1    10/2002

(Continued)

OTHER PUBLICATIONS

A-T Surgical Mfg. Co., Inc., "A-T Nasogastric Tube Holder" product packaging (undated).

(Continued)

*Primary Examiner* — Patricia Bianco
*Assistant Examiner* — Keri J Nelson
(74) *Attorney, Agent, or Firm* — Finnegan, Henderson, Farabow, Garrett & Dunner, LLP

(57) ABSTRACT

A tube holder assembly is provided for securing a medical tube such as an endotracheal tube to a patient. In one illustrative embodiment, the holder assembly comprises a support strap for placement around the patient's head or neck region, a bracket for holding the endotracheal tube in position relative to the patient's mouth, and a face anchoring portion for securing the support strap to the patient's face region. The support strap includes a front surface and an opposed, back surface. The bracket may be attached to the front surface of the support strap. The bracket may include an upper bar and an arm extending from the upper bar. The face anchoring device may comprise a first surface configured to adhere to the patient's face region, and a second, opposed surface having a strap-engaging portion configured to mechanically engage the back surface of the support strap. The support strap may be configured to be repeatedly releasable and adjustable to the face anchoring device.

38 Claims, 11 Drawing Sheets

U.S. PATENT DOCUMENTS

| | | |
|---|---|---|
| 3,693,624 A | 9/1972 | Shiley et al. |
| 3,713,448 A | 1/1973 | Arrott |
| 3,726,280 A | 4/1973 | Lacount |
| 3,747,166 A | 7/1973 | Eross |
| 3,760,811 A | 9/1973 | Andrew |
| 3,978,854 A | 9/1976 | Mills, Jr. |
| 4,018,221 A | 4/1977 | Rennie |
| 4,059,105 A | 11/1977 | Cutruzzula et al. |
| 4,074,397 A | 2/1978 | Rosin |
| 4,088,136 A | 5/1978 | Hasslinger et al. |
| 4,096,863 A | 6/1978 | Kaplan et al. |
| 4,114,626 A | 9/1978 | Beran |
| 4,120,304 A | 10/1978 | Moor |
| 4,122,857 A | 10/1978 | Haerr |
| 4,136,848 A | 1/1979 | McCollum |
| 4,142,527 A | 3/1979 | Garcia |
| 4,161,946 A * | 7/1979 | Zuesse ............................ 602/36 |
| 4,165,748 A | 8/1979 | Johnson |
| 4,191,180 A | 3/1980 | Colley et al. |
| 4,215,687 A | 8/1980 | Shaw |
| 4,223,671 A | 9/1980 | Muto |
| 4,235,229 A | 11/1980 | Ranford et al. |
| 4,249,529 A | 2/1981 | Nestor et al. |
| 4,270,529 A | 6/1981 | Muto |
| D260,932 S | 9/1981 | Chodorow et al. |
| 4,308,642 A | 1/1982 | Heyman |
| 4,313,437 A | 2/1982 | Martin |
| 4,324,237 A | 4/1982 | Buttaravoli |
| 4,326,515 A | 4/1982 | Shaffer et al. |
| 4,331,143 A | 5/1982 | Foster |
| 4,331,144 A | 5/1982 | Wapner |
| D265,423 S | 7/1982 | Abraham et al. |
| 4,351,331 A | 9/1982 | Gereg |
| 4,367,735 A | 1/1983 | Dali |
| 4,378,012 A | 3/1983 | Brown |
| 4,392,857 A | 7/1983 | Beran |
| 4,406,283 A | 9/1983 | Bir |
| 4,416,664 A | 11/1983 | Womack |
| 4,437,463 A | 3/1984 | Ackerman |
| 4,442,456 A | 4/1984 | Iwata et al. |
| 4,445,894 A | 5/1984 | Kovacs |
| 4,447,238 A | 5/1984 | Eldridge, Jr. |
| 4,449,527 A | 5/1984 | Hinton |
| 4,449,975 A | 5/1984 | Perry |
| 4,457,754 A | 7/1984 | Buttaravoli |
| 4,460,356 A | 7/1984 | Moseley |
| 4,480,639 A | 11/1984 | Peterson et al. |
| 4,484,913 A | 11/1984 | Swauger |
| 4,490,141 A | 12/1984 | Lacko et al. |
| 4,502,478 A | 3/1985 | Lifton |
| 4,516,293 A | 5/1985 | Beran |
| 4,520,813 A | 6/1985 | Young |
| 4,520,815 A | 6/1985 | Marinoff |
| 4,530,354 A | 7/1985 | Froilan |
| 4,534,342 A | 8/1985 | Pexa |
| 4,534,762 A | 8/1985 | Heyer |
| 4,537,192 A | 8/1985 | Foster |
| 4,548,200 A | 10/1985 | Wapner |
| 4,569,348 A | 2/1986 | Hasslinger |
| 4,583,976 A | 4/1986 | Ferguson |
| 4,592,351 A | 6/1986 | Smith et al. |
| 4,617,017 A | 10/1986 | Hubbard et al. |
| 4,622,034 A | 11/1986 | Shattuck |
| 4,639,980 A | 2/1987 | Peterson |
| 4,649,913 A | 3/1987 | Watson |
| 4,655,209 A | 4/1987 | Scott |
| 4,658,814 A | 4/1987 | Anderson |
| 4,662,366 A | 5/1987 | Tari |
| 4,665,566 A | 5/1987 | Garrow |
| 4,671,787 A | 6/1987 | Widman |
| 4,683,882 A | 8/1987 | Laird |
| 4,702,736 A | 10/1987 | Kalt et al. |
| 4,706,662 A | 11/1987 | Thompson |
| 4,706,914 A | 11/1987 | Ground |
| 4,726,716 A | 2/1988 | McGuire |
| 4,737,143 A | 4/1988 | Russell |
| 4,738,662 A | 4/1988 | Kalt et al. |
| 4,744,358 A | 5/1988 | McGinnis |
| 4,774,944 A | 10/1988 | Mischinski |
| 4,774,946 A | 10/1988 | Ackerman et al. |
| 4,778,448 A | 10/1988 | Meer |
| 4,799,923 A | 1/1989 | Campbell |
| 4,804,374 A | 2/1989 | Laskody |
| 4,808,160 A | 2/1989 | Timmons et al. |
| 4,821,736 A | 4/1989 | Watson |
| 4,822,342 A | 4/1989 | Brawner |
| 4,823,789 A | 4/1989 | Beisang, III |
| 4,826,486 A | 5/1989 | Palsrok et al. |
| 4,836,200 A | 6/1989 | Clark |
| 4,838,878 A | 6/1989 | Kalt et al. |
| 4,840,617 A | 6/1989 | Osterholm |
| 4,844,061 A | 7/1989 | Carroll |
| 4,867,154 A | 9/1989 | Potter et al. |
| 4,906,234 A | 3/1990 | Voychehovski |
| 4,911,698 A | 3/1990 | Wapner |
| 4,932,943 A | 6/1990 | Nowak |
| 4,939,818 A | 7/1990 | Hahn |
| 4,944,310 A | 7/1990 | Sullivan |
| D310,721 S | 9/1990 | Beisang et al. |
| D312,880 S | 12/1990 | Bodai et al. |
| 4,974,593 A | 12/1990 | Ng |
| 4,976,700 A | 12/1990 | Tollini |
| 4,986,815 A | 1/1991 | Schneider |
| 4,988,338 A | 1/1991 | Taylor et al. |
| 4,997,421 A | 3/1991 | Palsrok et al. |
| 5,009,227 A | 4/1991 | Nieuwstad |
| 5,015,251 A | 5/1991 | Cherubini |
| 5,019,050 A | 5/1991 | Lynn et al. |
| 5,026,352 A | 6/1991 | Anderson |
| 5,037,397 A | 8/1991 | Kalt et al. |
| 5,038,778 A | 8/1991 | Lott |
| 5,042,477 A | 8/1991 | Lewis |
| 5,042,478 A | 8/1991 | Kopola et al. |
| 5,048,158 A | 9/1991 | Koerner |
| 5,060,645 A | 10/1991 | Russell |
| 5,069,206 A | 12/1991 | Crosbie |
| 5,076,269 A | 12/1991 | Austin |
| 5,098,399 A | 3/1992 | Tollini |
| 5,100,393 A | 3/1992 | Johnson |
| 5,101,822 A | 4/1992 | Kimmel |
| 5,104,076 A | 4/1992 | Goodall, Jr. |
| 5,105,807 A | 4/1992 | Kahn et al. |
| D326,916 S | 6/1992 | Briggs, III |
| 5,120,300 A | 6/1992 | Shaw |
| 5,134,995 A | 8/1992 | Gruenke et al. |
| 5,146,913 A | 9/1992 | Khorsandian et al. |
| 5,147,322 A | 9/1992 | Bowen et al. |
| 5,156,641 A | 10/1992 | White |
| 5,167,050 A | 12/1992 | Korsen |
| 5,167,630 A | 12/1992 | Paul |
| 5,172,688 A | 12/1992 | Dillon |
| 5,174,483 A | 12/1992 | Moore, IV et al. |
| 5,188,101 A | 2/1993 | Tumolo |
| 5,200,245 A | 4/1993 | Brodrick, Jr. |
| 5,205,832 A | 4/1993 | Tuman |
| 5,214,874 A | 6/1993 | Faulkner |
| 5,237,988 A | 8/1993 | McNeese |
| 5,244,464 A | 9/1993 | Madden et al. |
| 5,261,893 A | 11/1993 | Zamierowski |
| 5,263,941 A | 11/1993 | Cockrill |
| 5,271,745 A | 12/1993 | Fentress et al. |
| 5,284,469 A | 2/1994 | Jasen et al. |
| 5,295,480 A | 3/1994 | Zemo |
| 5,304,146 A | 4/1994 | Johnson et al. |
| 5,305,742 A | 4/1994 | Styers et al. |
| 5,306,233 A | 4/1994 | Glover |
| 5,308,339 A | 5/1994 | Kalt et al. |
| 5,341,802 A | 8/1994 | Calebaugh |
| 5,342,317 A | 8/1994 | Claywell |
| 5,345,931 A | 9/1994 | Battaglia, Jr. |
| 5,352,209 A | 10/1994 | Bird et al. |
| 5,357,952 A | 10/1994 | Schuster et al. |
| 5,362,303 A | 11/1994 | Jasen et al. |
| 5,368,023 A | 11/1994 | Wolf |
| 5,368,024 A | 11/1994 | Jones |
| D354,812 S | 1/1995 | Jasen et al. |
| 5,395,344 A | 3/1995 | Beisang, III et al. |

| | | |
|---|---|---|
| 5,397,639 A | 3/1995 | Tollini |
| 5,402,776 A | 4/1995 | Islava |
| 5,411,484 A | 5/1995 | Shattuck |
| 5,419,319 A | 5/1995 | Werner |
| 5,421,327 A | 6/1995 | Flynn et al. |
| 5,433,359 A | 7/1995 | Flowers |
| 5,437,273 A | 8/1995 | Bates et al. |
| 5,438,979 A | 8/1995 | Johnson, Jr. et al. |
| 5,448,985 A | 9/1995 | Byrd |
| 5,451,725 A | 9/1995 | Goldman |
| 5,468,229 A | 11/1995 | Chandler |
| 5,468,231 A | 11/1995 | Newman et al. |
| 5,471,980 A | 12/1995 | Varner |
| 5,474,063 A | 12/1995 | Riendeau |
| 5,477,852 A | 12/1995 | Landis et al. |
| 5,480,719 A | 1/1996 | Tollini |
| 5,484,420 A | 1/1996 | Russo |
| 5,485,837 A | 1/1996 | Solesbee et al. |
| 5,490,504 A | 2/1996 | Vrona et al. |
| 5,496,282 A | 3/1996 | Militzer et al. |
| 5,501,216 A | 3/1996 | Byrd |
| 5,507,285 A | 4/1996 | Mota |
| 5,513,633 A | 5/1996 | Islava |
| 5,529,062 A | 6/1996 | Byrd |
| 5,535,739 A | 7/1996 | Rapoport et al. |
| 5,542,128 A | 8/1996 | Lomas |
| 5,546,933 A | 8/1996 | Rapoport et al. |
| 5,546,938 A | 8/1996 | McKenzie |
| 5,551,421 A | 9/1996 | Noureldin et al. |
| 5,555,881 A | 9/1996 | Rogers et al. |
| 5,558,090 A | 9/1996 | James |
| 5,638,814 A | 6/1997 | Byrd |
| 5,653,232 A | 8/1997 | Rogers et al. |
| 5,664,581 A | 9/1997 | Ashley |
| 5,671,732 A | 9/1997 | Bowen |
| 5,676,136 A | 10/1997 | Russo |
| 5,682,881 A | 11/1997 | Winthrop et al. |
| 5,685,292 A | 11/1997 | Fenn |
| 5,704,916 A | 1/1998 | Byrd |
| 5,709,665 A | 1/1998 | Vergano et al. |
| 5,716,347 A | 2/1998 | Gibbs |
| 5,718,691 A | 2/1998 | Russo |
| 5,720,734 A | 2/1998 | Copenhaver et al. |
| D393,310 S | 4/1998 | Russo |
| 5,735,272 A | 4/1998 | Dillon et al. |
| 5,735,822 A | 4/1998 | Steins |
| 5,743,885 A | 4/1998 | Hoerby |
| 5,752,511 A | 5/1998 | Simmons et al. |
| 5,755,225 A | 5/1998 | Hutson |
| 5,782,236 A | 7/1998 | Ess |
| 5,785,690 A | 7/1998 | Newman et al. |
| 5,786,062 A | 7/1998 | Callahan, Jr. et al. |
| 5,795,334 A | 8/1998 | Cochrane, III |
| 5,797,394 A | 8/1998 | Boyd |
| 5,797,884 A | 8/1998 | Byrd |
| 5,803,079 A | 9/1998 | Rogers et al. |
| 5,833,663 A | 11/1998 | Bierman et al. |
| 5,839,437 A | 11/1998 | Briggs, III |
| 5,845,643 A | 12/1998 | Vergano et al. |
| 5,868,132 A | 2/1999 | Winthrop et al. |
| 5,870,849 A | 2/1999 | Colson, Jr. |
| 5,879,335 A | 3/1999 | Martinez et al. |
| 5,897,519 A | 4/1999 | Shesol et al. |
| 5,931,854 A | 8/1999 | Dillon |
| 5,934,276 A | 8/1999 | Fabro et al. |
| 5,941,856 A | 8/1999 | Kovacs et al. |
| 6,009,872 A | 1/2000 | Delaplane et al. |
| 6,015,119 A | 1/2000 | Starchevich |
| 6,050,263 A | 4/2000 | Choksi et al. |
| 6,067,985 A | 5/2000 | Islava |
| 6,068,649 A | 5/2000 | Chamberlain |
| 6,117,086 A | 9/2000 | Shulze |
| 6,132,398 A | 10/2000 | Bierman |
| 6,142,953 A | 11/2000 | Burton et al. |
| 6,165,168 A | 12/2000 | Russo |
| 6,261,277 B1 | 7/2001 | Osborn, III et al. |
| 6,296,164 B1 | 10/2001 | Russo |
| 6,408,850 B1 | 6/2002 | Sudge |
| 6,419,660 B1 | 7/2002 | Russo |
| 6,526,978 B2 | 3/2003 | Dominguez |
| 6,561,192 B2 | 5/2003 | Palmer |
| 6,578,576 B1 | 6/2003 | Taormina et al. |
| 6,634,359 B1 | 10/2003 | Rudy, Jr. et al. |
| 6,810,878 B2 | 11/2004 | Palmer |
| 6,840,238 B2 | 1/2005 | Van Hegelsom |
| 2001/0029954 A1* | 10/2001 | Palmer ..................... 128/207.17 |
| 2002/0072656 A1 | 6/2002 | Vantassel et al. |
| 2002/0143296 A1 | 10/2002 | Russo |
| 2004/0094161 A1 | 5/2004 | Palmer |
| 2005/0171482 A1 | 8/2005 | Russo |
| 2005/0188993 A1 | 9/2005 | Steeves et al. |

FOREIGN PATENT DOCUMENTS

| | | |
|---|---|---|
| EP | 0 637 435 A1 | 2/1995 |
| GB | 2 235 629 A | 3/1991 |
| GB | 2 251 796 A | 7/1992 |
| WO | WO 90/06735 A | 6/1990 |
| WO | WO 97/12552 | 4/1997 |
| WO | WO 99/55410 | 11/1999 |
| WO | WO 2004/080518 | 9/2004 |

OTHER PUBLICATIONS

A-T Surgical Mfg. Co., Inc., "Suspensories," "Surgical Shield," "Catheter Leg Tube Holder," "Tracheostomy Tube Holder," "Catheter Waist Tube Holder," "Sweat Band," and "Nasogastric Tube Holder," product catalog (undated).

Ackrad Laboratories, Inc., "Comfit™ Endotracheal Tube Holder," product brochure (1995).

Ackrad Laboratories, Inc., "Comfit™ Endotracheal Tube Holder," product brochure (1999).

Advantage Medical, "Inside Advantage, Cath-Control™, catheter tube holder," product brochure (undated).

Ambu Inc., "Ambu® ET Tube Holder," product brochure (undated).

Anago®, "Cath-Control™ catheter anchor," product packaging (undated).

Ansley, a division of Struckmeyer, "tube holders," product brochures (undated).

B&B Medical Technologies, Inc., "B&B E.T. Tape" and "B&B E.T. Tape II," product brochures (undated).

B&B Medical Technologies, Inc., "B&B StabilTube," product brochure (undated).

B&B Medical Technologies, Inc., "B&B Lock-Tite," product brochure (undated).

B&B Medical Technologies, Inc., "B&B TrachGuard™," product information at http://www.bandb-medical.com (2005).

B&B Medical Technologies, Inc., "B&B Trachstay," product information at http://www.bandb-medical.com (2005).

B&B Medical Technologies, Inc., "Nasel E.T. Tape Kit™" and "Lock-Tite™," product advertisements (1996).

BrightWake Ltd., "tube holders," product information at http://www.brightwake.co.uk/sewn.html (2005).

Beiersdorf Inc., "Coverlet® Adhesive Dressings, Hospital Sizes (#1307 Used as N-G Holder)," product brochure (1990).

Biomedix, Inc., "EndoGrip™ Endotracheal Tube Holder," product brochure (1994).

Bird & Cronin, Inc., "Trach-Mate™ Tracheostomy Tube Holder," product information at http://www.birdcronin.com (2005).

Bruce Medical Supply, "Trach Tube Strap," product information at http://store.yahoo.com/brucemedical/trachtubestrap.html (2005).

Cooper Surgical, Inc., "Comfit™ Endotracheal Tube Holder," product information at http://www.coopersurgical.com (2005).

Cooper Surgical, Inc. (Ackrad Laboratories, Inc.), "Trake-fit™," product brochure (1997).

Custom Hospital Products, "Cotton Twill (Trach Tape)," "Trach Ties with Velcro," and "Tracheostomy Tube Ties," product catalog (undated).

DHD Healthcare, "DHD® Endotracheal Tube Holder," product brochure (2001).

DHD Healthcare, "DHD® Ventilator Support: Tracheostomy Strap," product information at http://www.dhd.com/catalog/ventilator/tracheostomyStraps.asp (2005).

DHD Healthcare, "Ventilator Support: Endotracheal Tube Holder Wrap Strap," product information at http://www.dhd.com/catalog/ventilator/endostrap.asp (2005).
DHD Healthcare, "DHD® Wrap Strap™ Endotracheal Tube Holder," product brochure (2001).
Dale Medical Products, Inc., "Dale® hug Hospital Utility Grip, product sheet No. 930, holds tubes and cords securely" (1980).
Deknatel, a division of Howmedica, Inc., "Naso-Gard™ Nasogastric Tube Holder," product brochure (undated).
EMS Medical, "Breeze Happy Holder," "Breeze Tracheostomy Tube Holder," "Breeze St. Marina Safety Net," "Breeze Endotracheal Tube Holder," and "Breeze Wet Protect" product information at http://www.ems-medical.co.uk/breeze.php (2005).
Encompas™ Unlimited, Inc., "Bite Blocks," product information at http://www.encompasunlimited.com (2005).
Encompas™ Unlimited, Inc., "Adult Bite Block," product information at http://www.encompasunlimited.com/store (2005).
Encompas™ Unlimited, Inc., "Adult Best Block," product information at http://www.encompasunlimited.com (2005).
International Search Report for PCT/US2005/044200, dated Apr. 3, 2006, Ex. Martine Eich.
ErgoMed, Inc., "Tube Tamer" and "Tube Restraint" product information at http://www.ergomed.com/TubeSecuringDevices.html (2005).
ErgoMed, Inc., "The Tube Tamer® B7013" product brochure (undated).
ErgoMed, Inc., "Trakeez" and "Trach Tamer," product information at http://www.ergomed.com/TubeSecuringDevices.html (2005).
E-Med Corporation, "Flexi-Trak™ Anchoring Device" product brochure (undated).
Genetic Laboratories Wound Care, Inc., "Cath-Strip™ Reclosable Catheter Fastener" product brochure (undated).
Genetic Laboratories Wound Care, Inc., "NG Strip™ Nasal Tube Fastener," product brochure (undated).
Genetic Laboratories Wound Care, Inc., "Percu-Stay Large Catheter and Tube Anchoring Device," product announcement (undated).
Genetic Laboratories Wound Care, Inc., "UC Strip™ Catheter Tubing Fastener," product brochure (undated).
Hollister, "Oral Endotracheal Tube Attachment Device (ETAD)," product information at http://www.hollister.com/us (2005).
Hollister, "E₀TAD Oral Endotracheal Tube Attachment Device" product brochure (undated).
Hudson RCI®, "Endotracheal Tube Holder," product brochure (1984) and product information at http://www.hudsonrci.com/Products (2005).
Hudson®, "Infant Nasal CPAP System," product brochure (1988).
Hy-Tape® International, "Hy-Tape®—The Original Pink Tape®," product information at http://www.hytape.com/hytape/Docs/endo.html (2005).
Kapitex Healthcare Limited, "Trachi-Hold tube holders," product information at http://www.kapitex.com/products/tracheostomy/products-trachi-hold1a.htm (2005).
R. Lewis, Inc., "Lewis Tube Holder™," product brochure (undated).
M.C. Johnson Co., Inc., "Cath-Secure® Multi-Purpose Tube Holder," product brochure and product wrappers (undated).
M.C. Johnson Co., Inc., "Cath-Secure®, New and Improved," product brochures (undated).
M.C. Johnson Co., Inc., "Cath-Secure Dual Tab™ Multi-Purpose Tube Holder," product brochures and product wrappers (undated).
M.C. Johnson Co., Inc., "NG Secure™ tube holder," product brochure (undated).
Marpac, Inc., "ET Adhesive Tape™," product information at http://www.marpac.biz/ettape.html (2005) and product brochure (2004).
Marpac, Inc., "Tracheostomy Collar™," product information at http://www.marpac.biz/collar.html (2004).
Medex, "SecureEasy®," and "Quickstrap™," product brochure (undated) and product information at http:/www.medex.com/Medex/Product_Catalog/Respiratory/Products (2005).
Mor-Mac, Inc., "Tube Guard®," product brochure (1987).
N-C-N Products Co., "C-N Endotracheal Tube Holder," product brochure (undated).
Nellcor, "Tracheostomy Tube Holder," product description at http://www.nellcor.com (2005).
Nellcor, "Tracheal Tube Restraint," product information at http://www.nellcor.com (2005).
Olympic Medical, "Olympic Endo-Lok™ Endotracheal Tube Holder," product brochure (undated), and product description at http://www.olymed.com/endo-lok.htm (2005).
Paraproducts.com, "Grip-Et™ Endotracheal Tube Holder," product information at http://www.paraproducts.com (2005).
Pepper Medical, "Tracheostomy Tube Neckband," "Ventilator Antidisconnect Device & Tracheostomy Tube Neckband," "Pediatric Tracheostomy Tube Neckband," and "Laryngoscope Handle & Disposable Fiber-Optic Blades," product brochure (undated) and product information at http://www.peppermedical.com/distitems.html (2005).
Pocket Nurse, "Adjustable Endotracheal Tube Holder," product brochure (undated).
Portex Limited/Smiths Industries Medical Systems, "Adult Oral Tracheal Tube Holder," product brochure (undated).
Portex Limited/Smiths Industries Medical Systems, "Portex Velcro® Tracheostomy Tube Holders," product information at http://www.portex.com (2005).
Posey Company, "Posey Foam Trach Ties," product information at http://www.posey.com (2005).
Precision Medical, "PM1110 Endotracheal Tube Holder," product information at http://www.precisionmedical.com/productpages/regaccess.asp (2004).
Rüsch, Inc., a Teleflex Company, "Soft Cushion Neck Band with adjustable velcro straps," product information at http://www.myrusch.com (2005).
Scott Specialties, Inc., "Scott Tube Holders," product brochure (undated).
Skil-Care™ Corporation, "Trach Tube Holders and Ties," product brochure (undated).
Tecnol, "Naso-Gastric Tube Holder" product brochure (undated).
STI Medical Products, "Thomas™ Endotracheal Tube Holder," product brochure (1999); and product information at http://www.stimedical.com/tube_holder.htm (2005).
TNT Moborg International Ltd., "Immobilé Sterile for Compliant Patient Line Control," product packaging (undated) and product advertising (1995).
Tecnol, Inc., "Secure-All™ Tube Holder," product brochures (undated) and "Tube-Control Plus™ with Hydrogel" product packaging (1994).
Trademark Medical Corporation, "Craig Tube Holder," product brochure (undated).
Transatlantic Handelsgesellschaft Stolpe & Co. mbH, "Transafix®," product brochure (1998).
Tyco Healthcare/Kendall, "Tracheostomy Care Trays," product information at http://www.kendallhq.com/catalog/printfriendly.asp (2004); Superior Healthcare Group, Inc. "tracheostomy care trays and tube holders" price list (1994); and "Tube Holder" product description (undated).
Venmark International, "NG Secure tube holder," product information (1995).
Welcon, Inc., "Trachtape® Endotracheal Tube Securing Device," "Economy Tracheostomy Tube Holder," and "Tracheostomy Tube Holder" product information at http://www.welcon.com/2700.htm (2005).
Welcon, Inc., "Trachtape™ Endotracheal Tube Securing Device," product brochure (undated).
XiMEDix, "Endo-Secure," product information at http://www.ximedix.com (2005); and product brochure (1996).
XiMEDix, "Trach-Secure™ Tracheostomy Tube Retaining Collar," product brochure (undated).
Zefon Medical Products, "K-Lok® Universal Securement Device," product packaging (undated).

\* cited by examiner

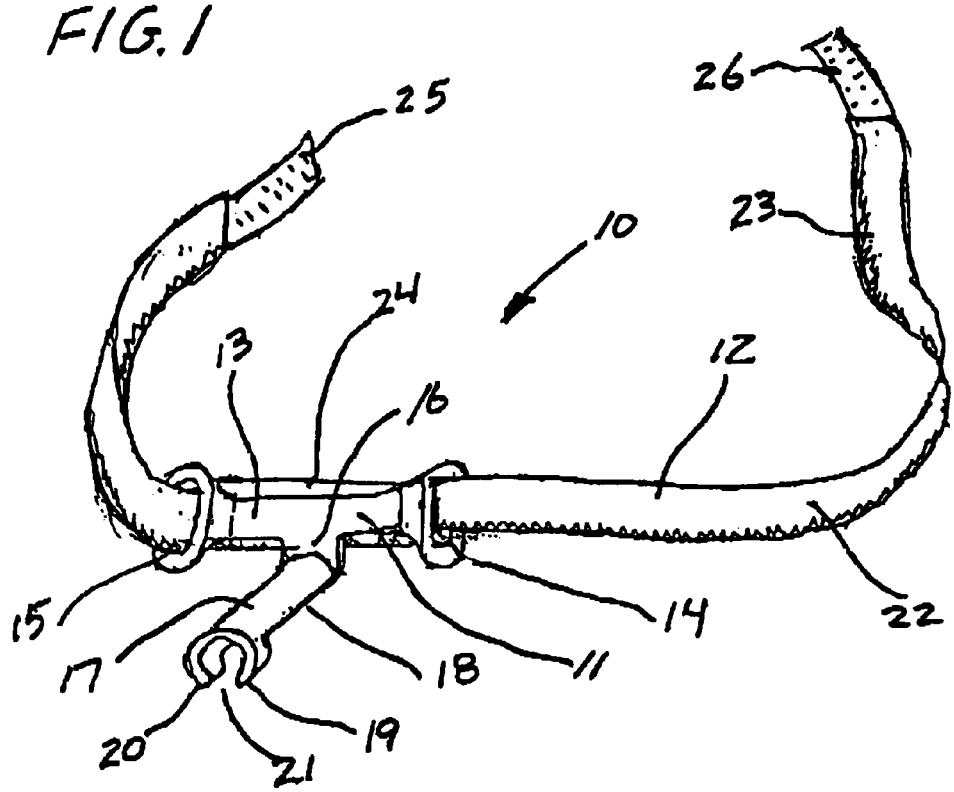
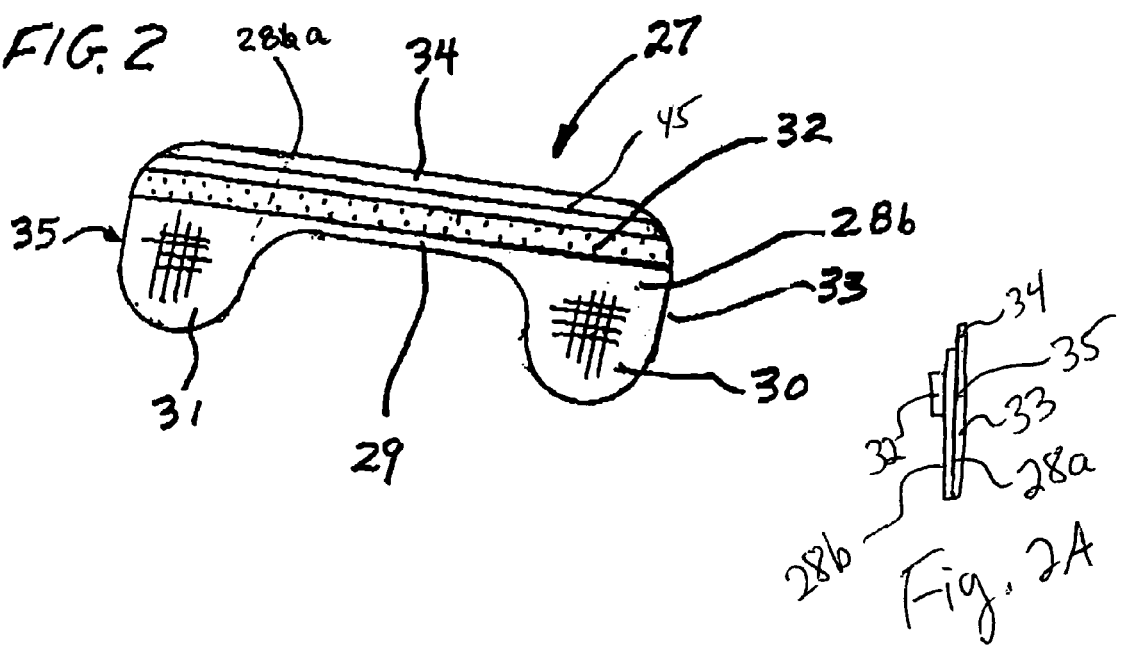

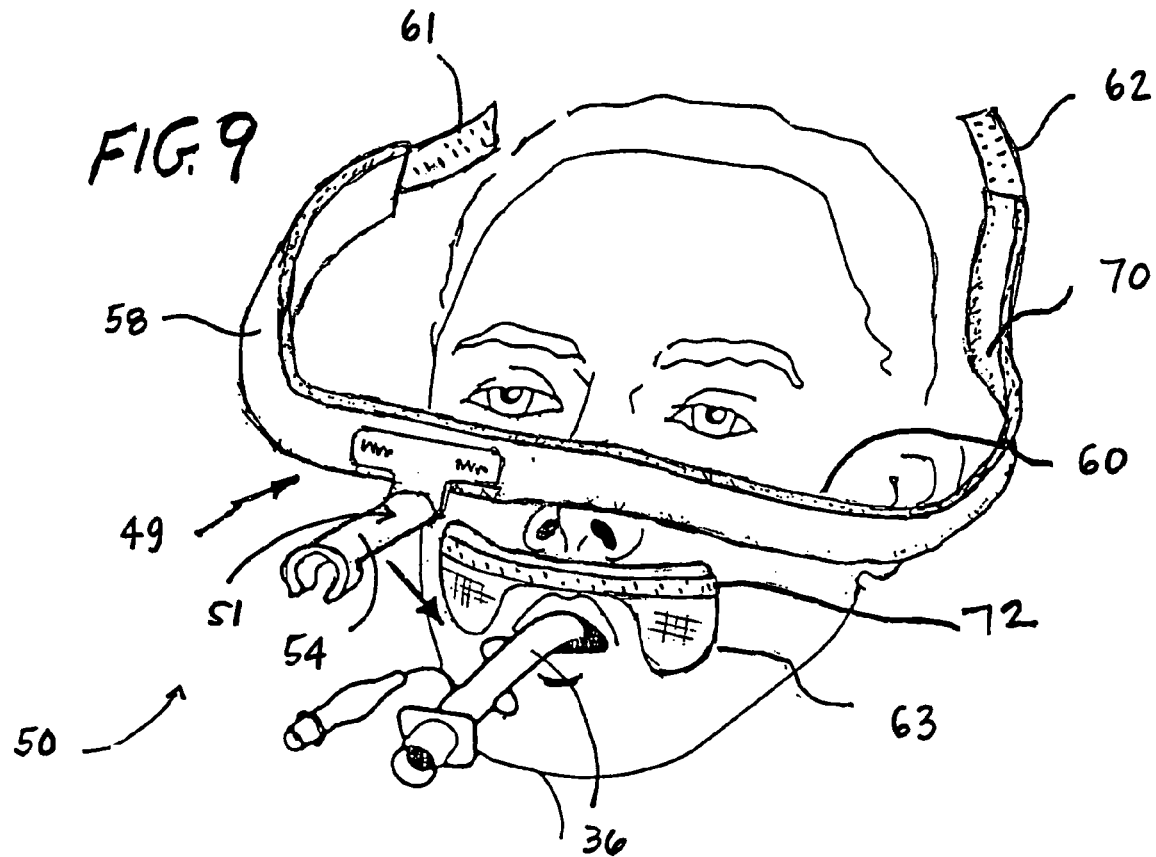
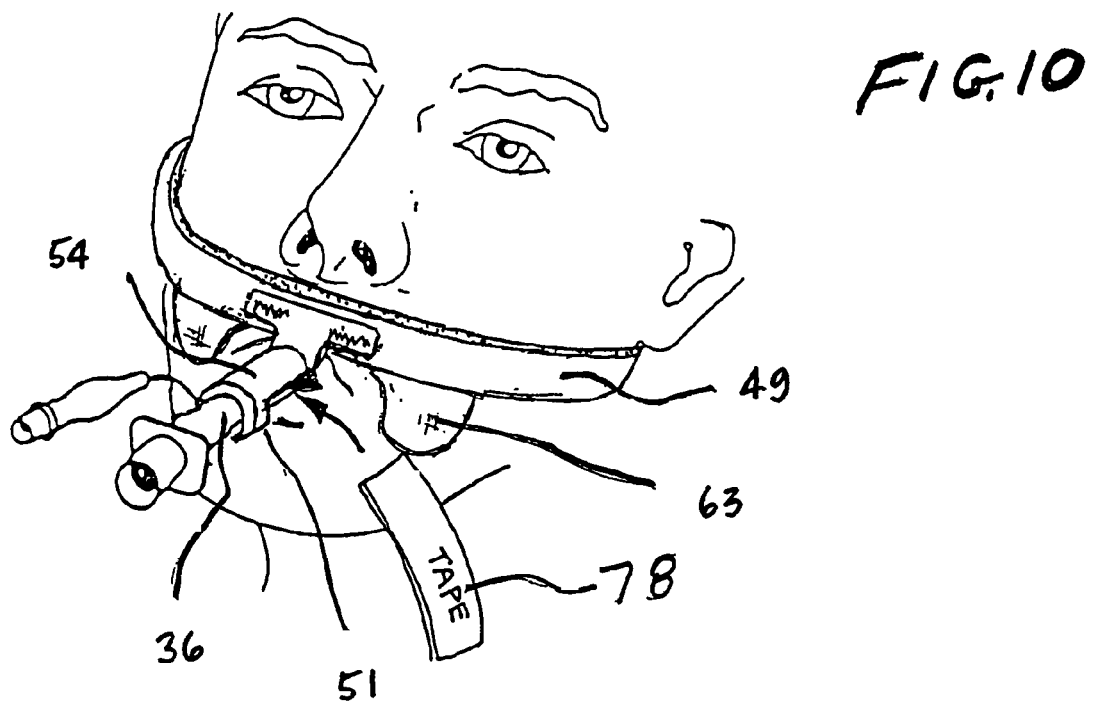

ENDOTRACHEAL TUBE HOLDER

CROSS-REFERENCE TO RELATED APPLICATIONS

This application claims priority to U.S. provisional application No. 60/632,806 filed on Dec. 3, 2004, the contents of which are hereby incorporated in its entirety by reference.

BACKGROUND

Endotracheal (ET) tubes are commonly used to ventilate patients for resuscitation, anesthesia and other critical care procedures. These patients are usually critically ill and unable to breathe on their own. Once inserted, it is desirable to secure the endotracheal tube in a fixed position to prevent movement of the tube or extubation of the tube from the patient's airway.

Traditionally, endotracheal tubes have been secured to the patient by placing adhesive tape on the tube and affixing it to the patient's cheek or face. In some cases twill ties have been used, either alone or in combination with adhesive tape. Commercially available adhesive tape-type products for use with an endotracheal tube holder tend to sag and lift off the patient's face after limited use. Further, because the tape must be removed frequently for suctioning and repositioning, considerable skin irritation and possible infection can occur. Endotracheal tube securing devices which incorporate a biteblock are also available, but have not received widespread acceptance since biteblocks tend to irritate the patient's mouth and tongue after a short period of use.

More importantly, the endotracheal tube is often connected to a heavy, bulky breathing circuit along with a closed tracheal suction catheter, which tends to place a significant load strain and tension, or pulling force, on the endotracheal tube securing device. Also, humidifiers, water condensate traps, and oxygen lines, which may be part of the breathing circuit, add to the weight and tension exerted on the endotracheal tube. In such cases, purely adhesive tape-type products cannot withstand the constant load strain, leading to the tube coming out of position, sagging, or kinking. This misplacement or deformation of the tube can cause the airway to become partially shut off and results in the loss or reduction of administered ventilation to the patient.

Likewise, a rigid bite block-type endotracheal tube securing device suffers from similar problems in that the tube tends to bend or kink at the securement junction where the tube connects to the ventilator circuit and/or catheter. Often, the suction catheter or ventilator circuit will need to be moved or adjusted, causing the kinking of the endotracheal tube due to the weight of the attached equipment and the failure of the securement junction to flex or bend in response to the clinician's manipulation of the equipment.

Accordingly, there is a need for a lightweight, comfortable, easy to use securing device for an endotracheal tube which does not require a bite block, yet will provide maximum tube security and prevents kinking.

SUMMARY OF THE INVENTION

One illustrative embodiment of the present invention provides a holder assembly for securing a medical tube, such as for example, an endotracheal tube, to a patient's mouth. The holder assembly comprises a support strap for placement around the patient's head or neck region, a bracket for holding the endotracheal tube in position relative to the patient's mouth, and a face anchoring portion for securing the support strap to the patient's face region. The support strap includes a front surface and an opposed, back surface. The bracket may be attached to the front surface of the support strap. The bracket may include an upper bar and an arm extending from the upper bar. The face anchoring device may comprise a first surface configured to adhere to the patient's face region, and a second, opposed surface having a strap-engaging portion configured to mechanically engage the back surface of the support strap. The support strap may be configured to be repeatedly releasable and adjustable to the face anchoring device.

In another exemplary embodiment, a holder assembly for securing an endotracheal tube to a patient's mouth is provided. The holder assembly may comprise a support strap for placement around the patient's head or neck region, a bracket for holding the endotracheal tube in position relative to the patient, and a face anchoring device configured to adhere to the patient's face region and attachable to the support strap for secure engagement of the strap to the patient's face region. The bracket may include an upper bar and an arm extending from the upper bar. The arm may terminate in a gripping region configured to form a snap-fitting engagement around the endotracheal tube.

In still yet another exemplary embodiment, a holder assembly for securing an endotracheal tube to a patient's mouth is provided. The holder assembly may comprise a support strap for placement around the patient's head or neck region, a bracket affixed to the support strap for holding the endotracheal tube in position relative to the patient, and a face anchoring device configured to adhere to the patient's face region and attachable to the support strap for secure engagement of the strap to the patient's face region. The bracket may comprise an upper bar and an arm extending generally perpendicular from the upper bar. The arm may terminate in a gripping region including tabs for forming a snap-fitting engagement around the endotracheal tube.

It is to be understood that both the foregoing general description and the following detailed description are exemplary and explanatory only, and are not restrictive of the invention, as claimed.

BRIEF DESCRIPTION OF THE DRAWINGS

The following drawings, which are incorporated in and constitute a part of this specification, illustrate several embodiments of the invention and together with the description, serve to explain the principles of the invention.

FIG. 1 is a perspective view of a bracket/neckband component of an exemplary endotracheal tube holder assembly, according to one embodiment consistent with the principles of the present invention.

FIG. 2 is a perspective view of the face adherent portion of the tube holder assembly of FIG. 1.

FIG. 2A is a side view of the face adherent portion of FIG. 2.

FIG. 9 is a perspective view of a partially assembled tube holder assembly of FIGS. 7 and 8.

FIG. 10 shows an assembly step of further securing a tube to a portion of the tube holder assembly of FIG. 9 using tape.

DETAILED DESCRIPTION

Figure 3:
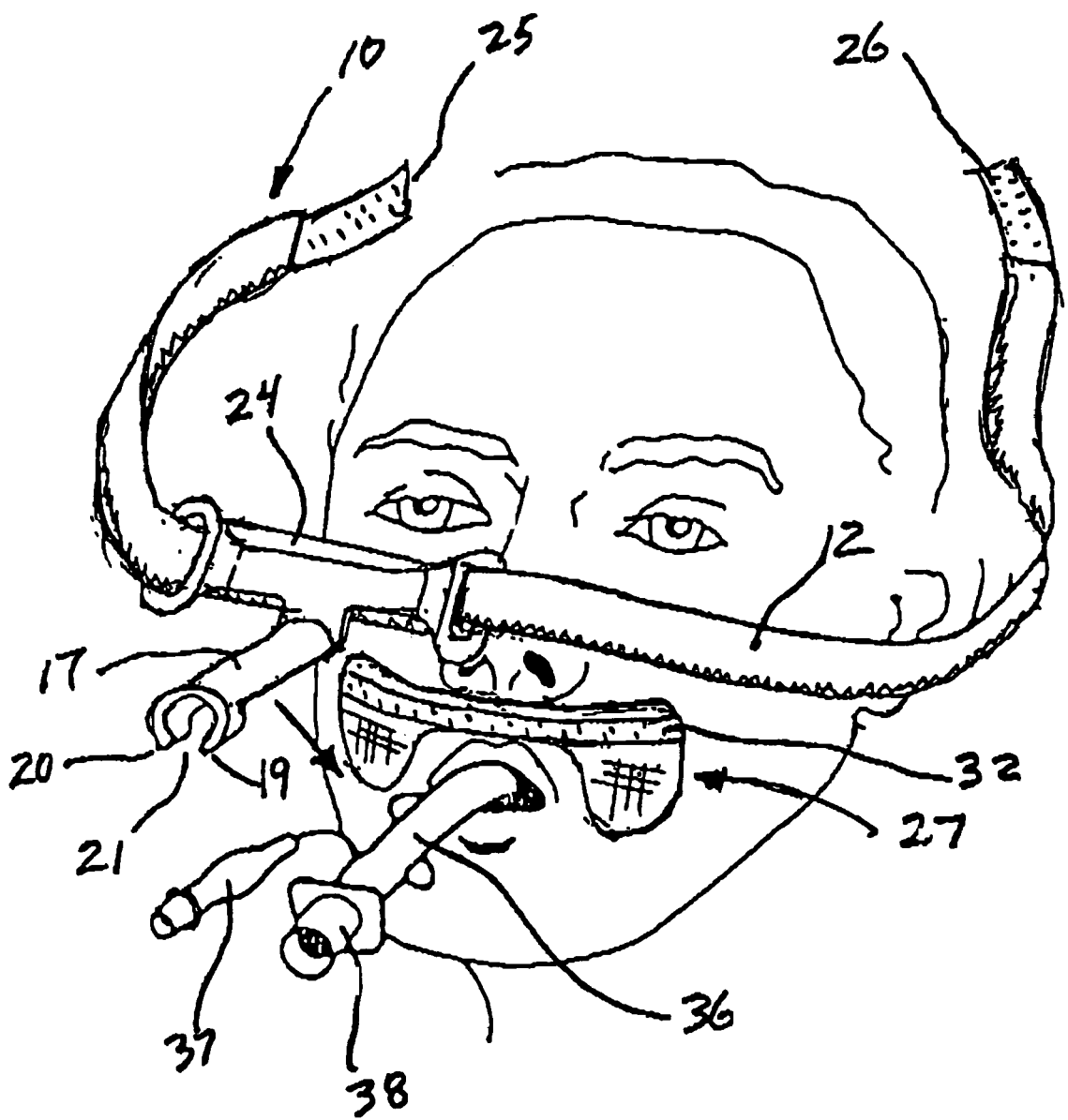
FIG. 3 is a perspective view of a partially assembled tube holder assembly of FIGS. 1 and 2.

A holder assembly is disclosed herein for securing a medical tube, such as for example, an endotracheal tube, to a patient. The holder assembly may comprise two or more components that cooperate to securely position an endotracheal tube against a patient's mouth. As shown in an exemplary embodiment depicted in FIG. 1, one component of the tube holder assembly 10 may include an elongated support strap or neckband 12 for placement around the patient's head or neck region. The support strap or neckband 12 may be made from a soft, comfortable yet strong material such as Velcro™ loop pile fabric which is flexible and comfortable. The neckband 12 may have a front surface 22 and an opposed, back surface 23, both made from Velcro™ loop pile fabric material. In one exemplary embodiment, the neckband 12 may be about 1 inch wide and about 30 inches long. Further, the neckband 12 may terminate at both ends into releasably attachable closure ends 25 and 26. These closure ends 25 and 26 may be sewn onto the neckband 12, and may include mechanical engagement surfaces for engaging the front surface 22 of the neckband 12. For example, the mechanical engagement surfaces may comprise Velcro™ hook fabric or material to interlock and engage the Velcro™ loop pile fabric of the front surface 22 of the neckband 12.

The tube holder assembly 10 may also comprise another component, such as a bracket 11, for holding the endotracheal tube in position relative to the patient's mouth. The bracket 11 may be, for example, a semi-flexible injection molded clear bracket 11. In one aspect, the bracket 11 may be injection molded in one piece from, for example, 95 shore A durometer semi-flexible blue tinted clear non-DEHP polyvinyl chloride (PVC) plastic, although other appropriate plastic materials may also be used. As shown in FIG. 1, the bracket 11 may include an upper bar 13 extending approximately four inches in total length and about ½ inch wide. Slots 14 and 15 may be provided at both ends of upper bar 13. These slots 14 and 15 may be molded with the upper bar 13, and in one embodiment may be dimensioned about ¾ inches high and about 0.200 inches wide.

Extending downward from upper bar 13 is a bridge 16 that can be, for example, about 0.500 inch wide. Projecting forwardly and outwardly from bridge 16 is a tube securing extension or arm 17 that can be, for example, about 1½ inches long. As illustrated, the arm 17 may extend generally perpendicular to the upper bar 13. The arm 17 may be integral with the upper bar 13, or alternatively, the arm 17 may be formed as a separate component. The extension or arm 17 may have a generally semi-circular contour with a built-in undercut portion 18 which terminates in a gripping region 21 comprising distal snap-in tabs 19 and 20 for snap-fitting engagement around the endotracheal tube. The tabs 19 and 20 may be flexible, and are configured to encircle a tube diameter of about 0.450 inches. Accordingly, the gripping portion 21 may accommodate all sizes of endotracheal tubes from size 5 up to size 10. The tabs 19 and 20 serve to snap over and retain the endotracheal tube onto the holder extension or arm 17. If desired, the extension or arm 17 may include a surface feature for enhanced engagement with the endotracheal tube and with an adhesive tape, if desired. For example, the surface feature may comprise a surface roughening, barbs, teeth, or adhesive on the undercut portion 18 or other surface contacting the endotracheal tube. In one aspect, the surface roughening may comprise about a 0.003 inch deep pebble finished texture molded onto the surface, which forms a friction fit non-slip engagement with the endotracheal tube along with an added gripping surface for optional placement of the adhesive tape.

As illustrated in FIG. 1, the neckband 12 may be threaded through dual slots 14 and 15 of the bracket 11 such that a portion 24 of the support strap 12 rests behind the upper bar 13 and the bracket 11 is attached to the front surface 22 of the support strap or neckband 12. In the embodiment shown, the neckband 12 can slide and be adjusted through the bracket 11 by way of dual slots 14 and 15 until the bracket 11 is centrally located on support strap 12. Alternately, the bracket 11 may also be affixed to the neckband 12, such as for example, by sewing the bracket 11 to the front surface 22 of the support strap 12.

FIGS. 2 and 2A illustrate yet another component of the tube holder assembly 10 comprising a face anchoring device 27 that cooperates with the support strap or neckband 12 to maintain the endotracheal tube in position relative to the patient's mouth. In one aspect, the face anchoring device 27 may be formed from a woven skin-colored fabric material, such as for example, Bioflex™ material 715P manufactured by Scapa Corp. The device 27 may be, for example, about 6 inches long and may comprise a central band portion 29 with cheek pads 30 and 31 on either side of the central band portion 29. The device 27 may comprise a first surface 28a configured to adhere to the patient's face region, and a second, opposed surface 28b having a strap-engaging portion configured to mechanically engage the back surface 23 of the support strap 12 for securing the strap 12 to the patient's face region. As shown in FIG. 2, the second surface 28b may include a Velcro™ hook strip 32 about ⅜ inch wide. This hook strip 32 serves as a complementary mating element to the mating element or Velcro™ loop pile fabric on the back surface 23 of the neckband 12, forming an interlocking relationship between the two. The first surface 28a of the device 27 may include a release liner 33 which can extend to upper extended release liner 34, which extends past the upper edge 45 of surface 28b to better enable gripping of the release liner. Once the extended release liner 34 is peeled back, it exposes skin-friendly adhesive 35 on the first surface 28a of the device 27. It should be noted that a crack and peel release liner can easily be substituted for the extended release liner 34, if desired. In another aspect, the face anchoring device 27 may be die cut to its final shape, as shown.

FIG. 3 depicts a partially assembled view of the tube holder assembly 10 of FIGS. 1 and 2. A face anchoring device 27 has been adhered to the patient's face region, as shown. In this embodiment, the Velcro™ hook strip 32 part of the device 27 extends the full width of the device 27. The portion 24 of neckband 12 behind the bracket 11, made from Velcro™ loop pile material, may be placed directly onto the mating Velcro™ hook strip 32 of the face anchoring device 27. The endotracheal tube 36 may be snapped onto the bracket extension or arm 17 such that the snap-in tabs 19 and 20 engage around the endotracheal tube 36 (including the pilot balloon tube 37 part of the tube 36). In this manner, the neckband 12 may form an interlocking, strong mechanical connection with the mating hook strip 32 on the face anchoring device 27. Such a configuration enables the support strap 12 to be repeatedly releasable and adjustable with respect to the face anchoring device 27. As shown, the endotracheal tube 36 may terminate with a standard adapter 38.

Figure 4:
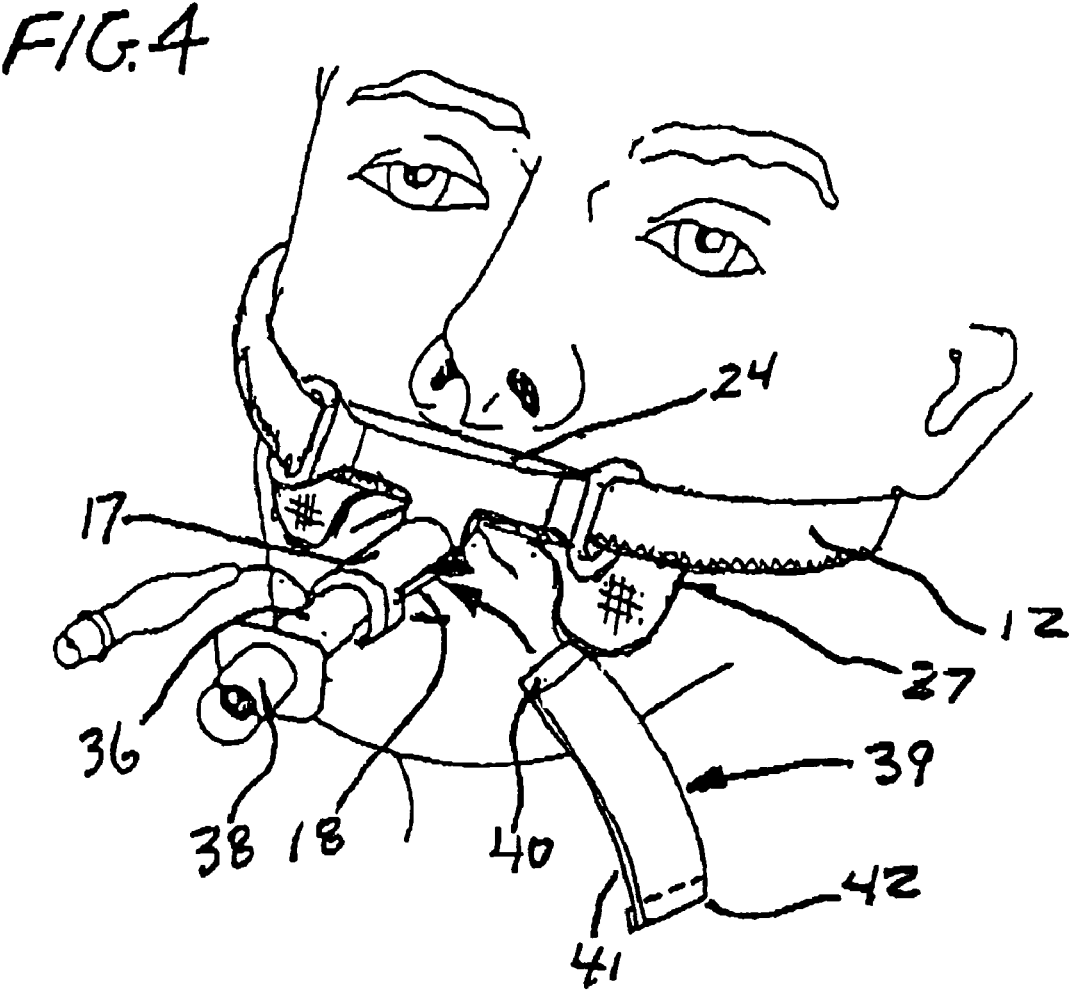
FIG. 4 shows an assembly step of further securing a tube to a portion of the tube holder assembly of FIG. 3 using tape.

For additional reinforcement, tape may be applied around the endotracheal tube 36 and the extension or arm 17, as shown in FIG. 4. For example, a foam tape 39 having an extended release liner 40 at one end and a non-adherent mylar tab 42 at another end may be applied. Once the liner 40 is peeled back it exposes an adhesive 41 which may be used to wrap the tube 36 around the bracket extension or arm 17 at undercut portion 18. Thus, the foam tape 39 securely adheres to both the bracket extension 17 and tube 36.

Figure 5:
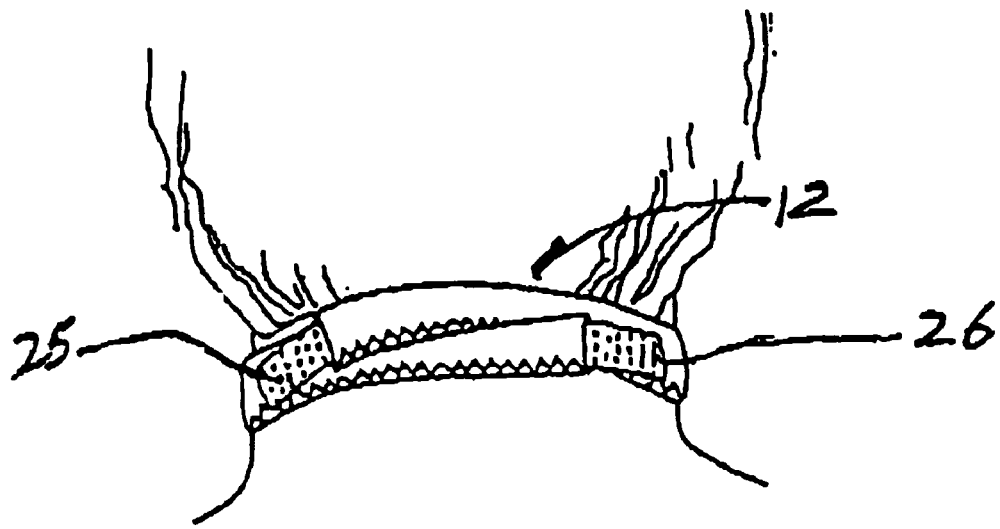
FIG. 5 is a rear view of the tube holder assembly of FIG. 4 depicting the support strap around a patient's neck.

Once the endotracheal tube 36 is in place, the closure ends 25 and 26 of the support strap 12 may be secured onto the front surface 22 of the strap 12, as shown in FIG. 5. As illustrated, the end of the strap 12 may be secured in an interlocking, crisscross arrangement to form a tight, secure fit behind the neck or head region of the patient. The closure ends 25 and 26 can easily be lifted off neckband 12 for easy adjustment of the tightness of the neckband 12.

Figure 6:
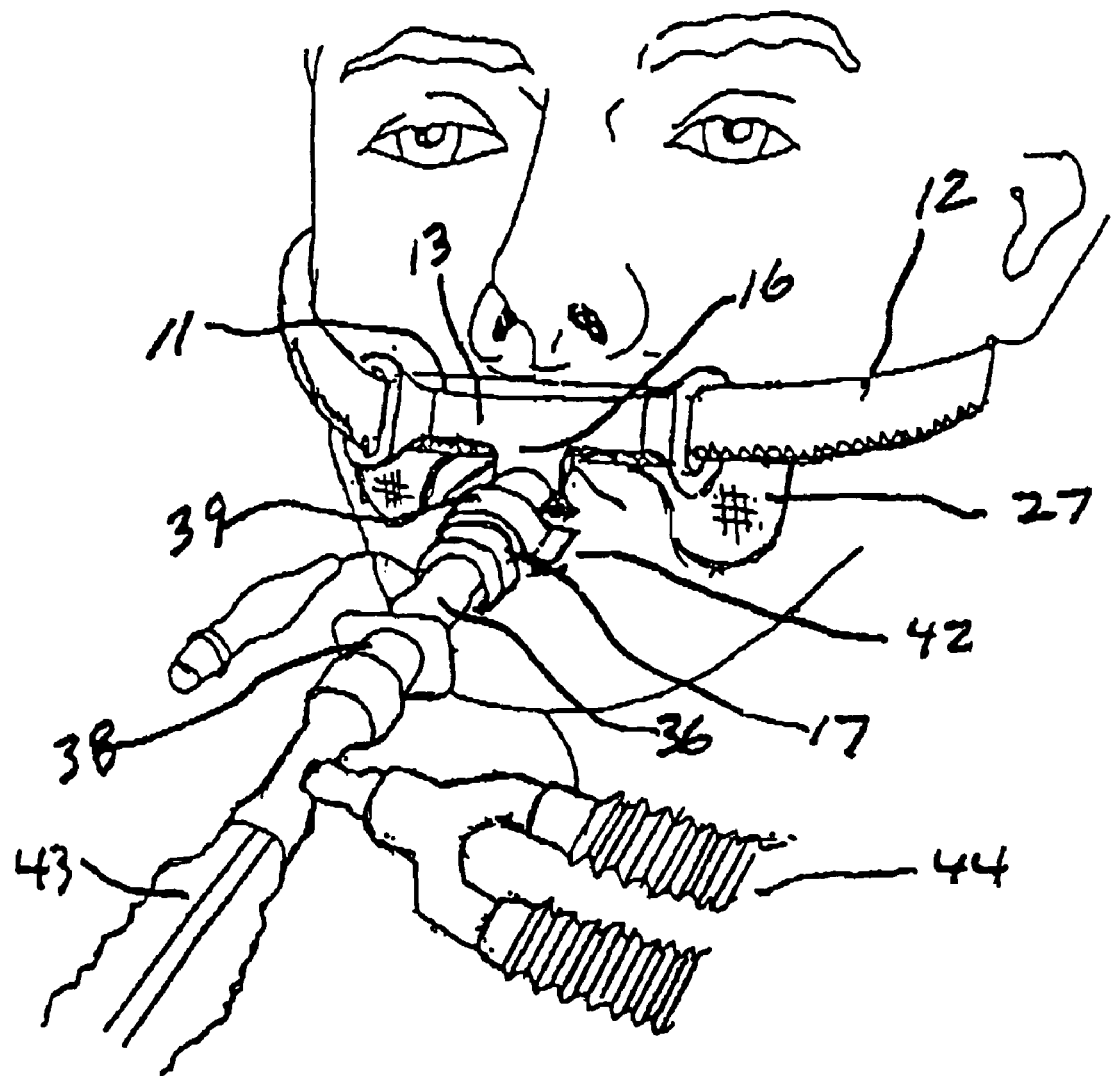
FIG. 6 is a perspective view of a fully assembled endotracheal tube holder assembly of FIG. 1 relative to a patient and being connected with other ventilation circuit equipment.

FIG. 6 shows a fully assembled tube holder assembly 10 comprising a neckband 12 adhered to a face anchoring device 27 with foam tape 39 wrapped around the bracket arm 17. Once assembled, the neckband 12 can remain securely fixed to the face anchoring device 27 to prevent any dislodgement or movement of the endotracheal tube 36. The crisscross arrangement of the ends of the neckband 12, as shown in FIG. 5, further prevents any load strain or tension acting to pull out the tube 36 from the mouth or airway of the patient. It is contemplated that the bridge 16 extending from the upper bar 13 of the bracket 11 will act as a pivot point such that the extension or arm 17 can flex slightly from side to side without kinking the endotracheal tube 36. Unlike with rigid extensions or arms on bite blocks of prior art devices, the bridge 16 of the present invention prevents the endotracheal tube 36 from bending or kinking. Further, it is contemplated that the heavy weight of a closed tracheal suction catheter 43 and connected ventilation circuitry, as partially depicted, will not pull out the endotracheal tube 36 with the use of this tube holder assembly 10. If repositioning of the endotracheal tube 36 is desired, the closure ends 25 and 26 on the neckband 12 and the portion 24 of the strap 12 behind the bracket 11 can be released and, as such, repeatedly repositioned as desired.

In addition, the lift tab 42 on the foam tape 39 can provide a convenient, easy manner for removal of the tape 39 from the extension or arm 17. The endotracheal tube 36 can be repositioned inward or outward from the trachea as needed, and a new piece of foam tape 39 or other suitable hospital-supplied tape can be used to resecure the tube 36 to the extension or arm 17. As such, the endotracheal tube 36 can be repositioned easily while providing easy access to the oral cavity of the patient for care or suctioning.

Figure 7:
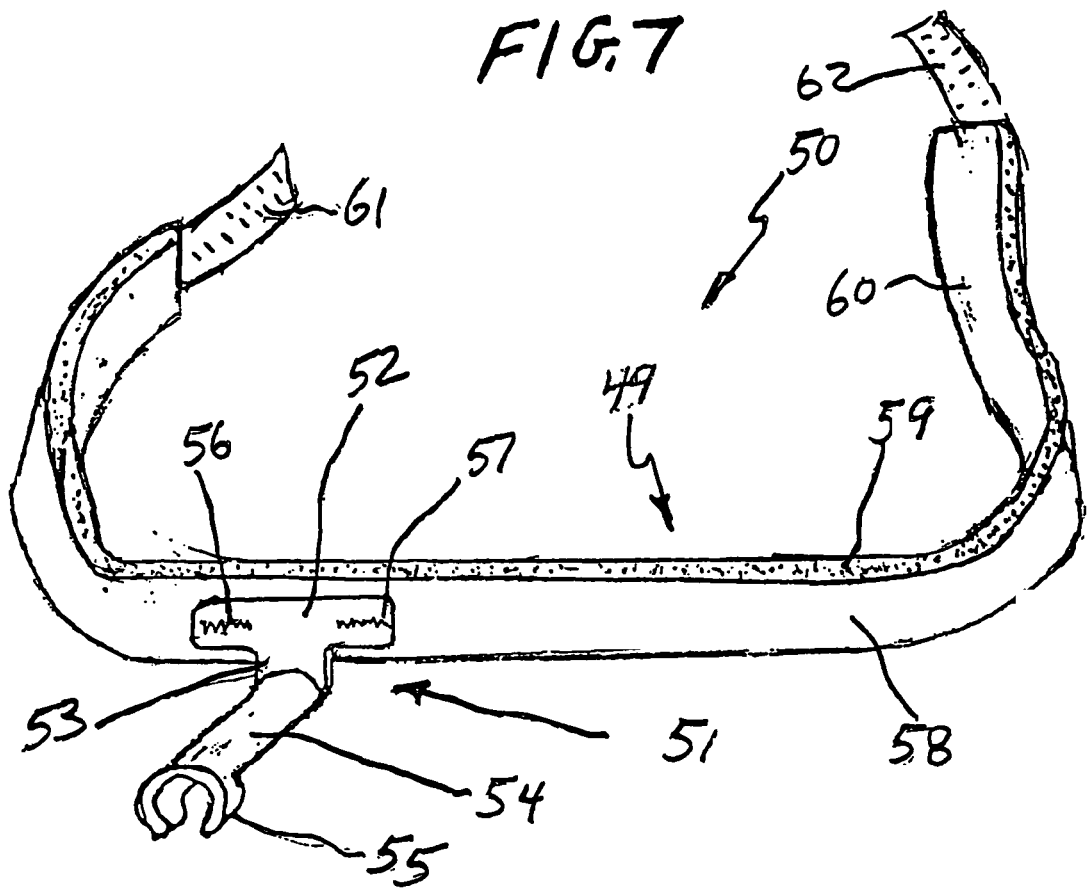
FIG. 7 is a perspective view of a bracket/neckband component of an exemplary endotracheal tube holder assembly, according to another embodiment consistent with the principles of the present invention.

FIG. 7 illustrates a component of another exemplary embodiment of a tube holder assembly 50 in accordance with the present invention. As shown, the component comprises a neckband or support strap 49 and a bracket 51 affixed to the strap 49. The neckband 49 may be formed of a soft, plush nylon tricot loop material on a front surface 58 and opposed, back surface 60. Sandwiched between both front and back surfaces 58 and 60 there can be provided a cushioned polyurethane foam core 59. Like the neckband 12 of FIG. 1, the neckband 49 may terminate into closure ends 61 and 62 comprising Velcro™ hook material. Unlike in FIG. 1, the bracket 51 of the present embodiment may be permanently affixed onto the support strap or neckband 49 by side stitching, such as for example, through the upper bar 52 at locations 56 and 57. The bracket 51 may be centrally located on the neckband 49 so as to form a unitary component of the tube holder assembly 50.

In one aspect, the bracket 51 may be a one-piece injection molded bracket 51 formed from blue tinted clear non-DEHP polyvinyl chloride plastic with a slightly softer more flexible durometer of 85 shore A. The bracket 51 may be similar to bracket 11, and can include an upper bar 52 dimensioned about 0.500 inches wide by about 2 inches long and about 0.070 inches in thickness. Downwardly extending from the upper bar 52 is a bridge 53 which extends into extension or arm 54. As illustrated, the arm 54 may extend generally perpendicular to the upper bar 52 and terminate in a gripping region comprising flexible tabs 55 to allow a snap-fitting engagement of the endotracheal tube 36 to the arm 54. The arm 54 may be integral with the upper bar 52, or alternatively, may be formed as a separate component. Like the extension or arm 17 of FIG. 1, the arm 54 may have a generally semicircular contour with a built-in undercut portion that may include a surface feature for enhanced engagement with the endotracheal tube. For example, the surface feature may comprise a surface roughening, barbs, teeth, or adhesive.

Figure 8:
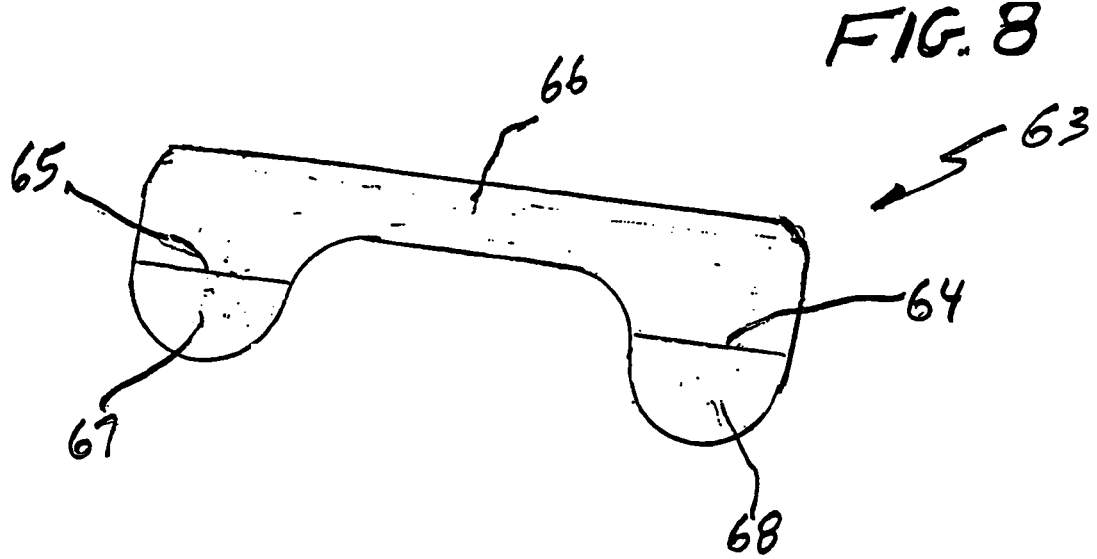
FIG. 8 is a rear view of a face adherent portion of the tube holder assembly of FIG. 7.

FIG. 8 illustrates a rear view of a face anchoring device 63 similar to the face anchoring device 27 of FIG. 1 for use with the tube holder assembly 50 of the present invention. The face anchoring device 63 may have dual crack and peel score lines 64 and 65 which permit convenient removal of a top release liner portion 66, leaving lower portions 67 and 68 for easy positioning using gloved hands by the clinician. This makes for convenient positioning and adherence of the face anchoring device 63 to the patient's face region.

FIG. 9 shows a partially assembled tube holder assembly 50 of FIG. 7 in accordance with an exemplary embodiment of the present invention. A face anchoring device 63 has been adhered to the patient's face region, as shown. As with face anchoring device 27, a Velcro™ hook strip 72 may extend across the width of the device 63. The back surface 60 of the neckband 49, comprising a mating element of Velcro™ loop pile material 70, may be placed onto the complementary mating element or hook strip 72 of the face anchoring device 63. The endotracheal tube 36 may be snap-fitted onto the arm 54 of the bracket 51 in a manner similar to what was described for FIG. 3. As shown in FIG. 10, for additional reinforcement tape 78 may be applied around the endotracheal tube 36 and the extension or arm 54. Any readily available hospital tape such as Durpore or Transpore may be used to wrap around bracket extension 54 to securely retain the endotracheal tube 36 in place.

Figure 11:
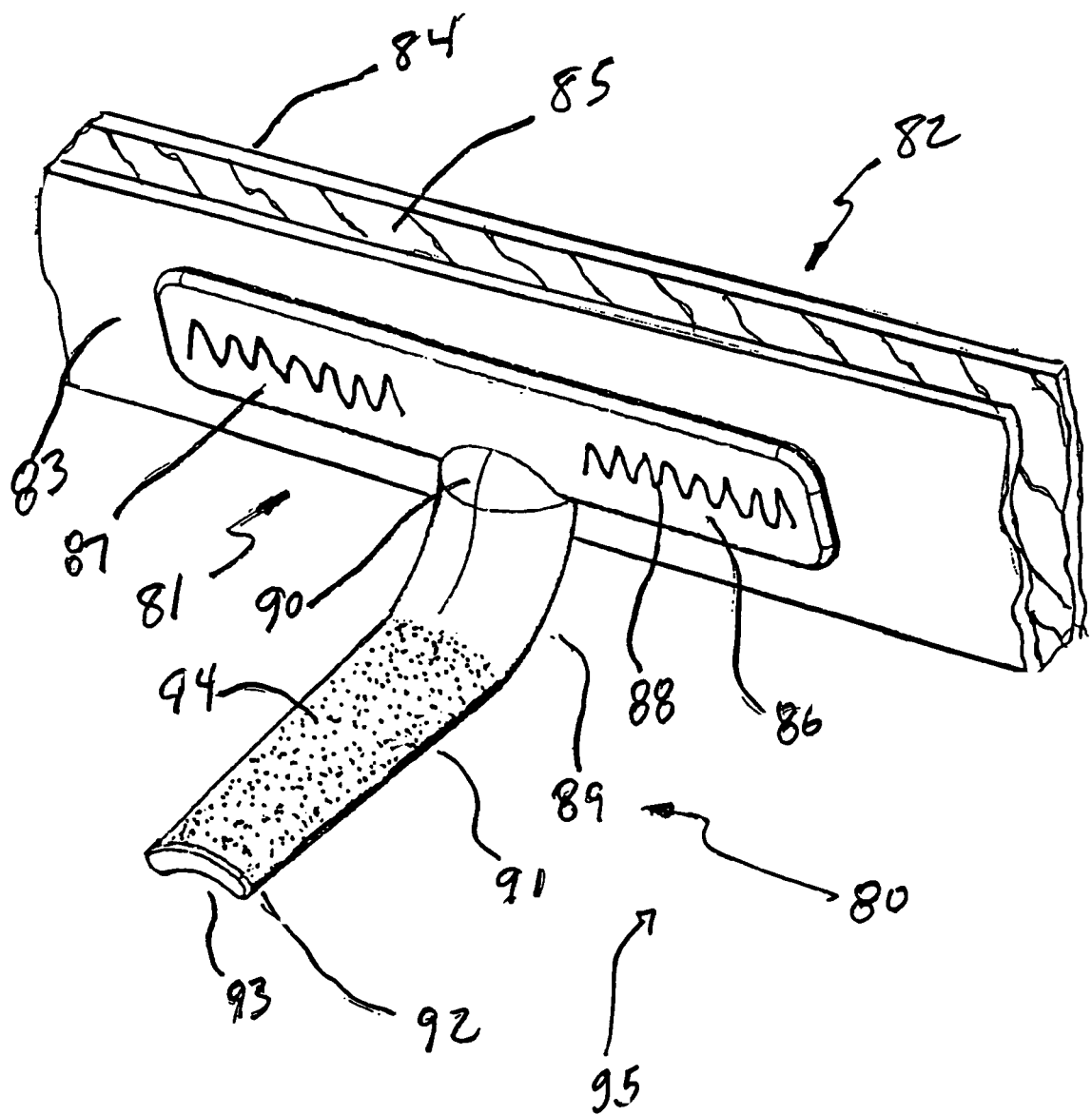
FIG. 11 is a perspective view of a bracket/neckband component of an exemplary endotracheal tube holder assembly, according to still another embodiment consistent with the principles of the present invention.

FIG. 11 depicts another embodiment of a bracket/neckband component of a tube holder assembly comprising a one-piece flexible PVC injection molded bracket 81 stitched onto a cushioned neckband 82. The neckband 82 comprises front and back surfaces 83 and 84 formed of Velcro™ loop pile material, with a central polyurethane soft cushioned core 85 in between. The bracket 81 may include an upper bar 86 which can be stitched at locations 87 and 88 to the neckband 82. Further, the bracket 81 can be configured to include a forwardly and outwardly extending curved bridge portion 89 which eliminates any direct pressure point of contact with the upper lip of the patient. A molded-in fillet 90 may also be provided and acts as a stabilizing fixture between the flat upper bar 86 and the curved bridge portion 89, reinforcing both elements.

As illustrated, projecting forward from the bridge portion 89 can be a tapered extension 91, which tapers from a dimension of about 0.500 inches at the bridge portion 89 to about 0.400 inches at its distal tip 92. The length of the extension can be about 1.125 inches, which is long enough to accept a standard 1" wide hospital tape. The extension or arm 91 may have a uniformed, slightly curved underside 93 which can mate with the contours of adult endotracheal tubes from about 6 mm up to 10 mm in size. The top surface 94 of the extension 91 may have a molded-in textured pebble surface which provides a better gripping surface for placement of hospital tape compared to a typical, smooth molded surface.

Figure 12:
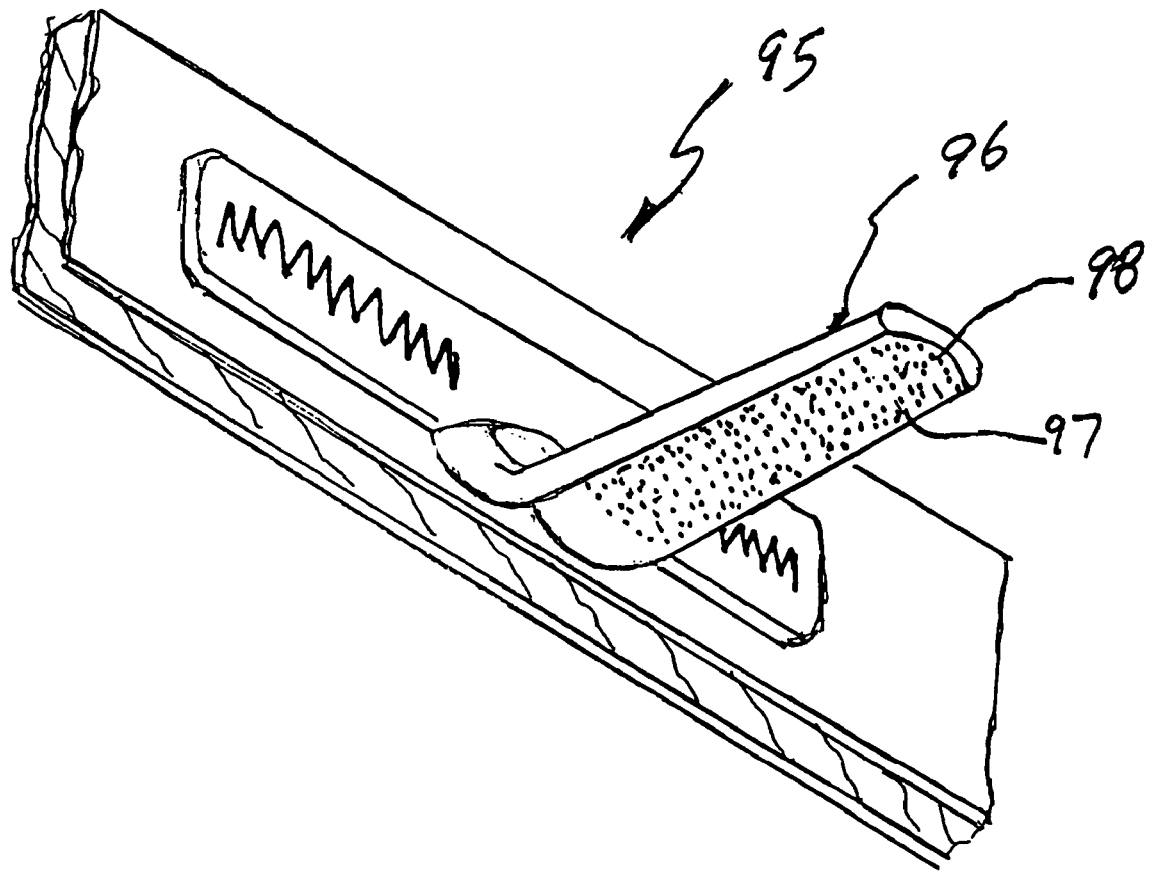
FIG. 12 is an underside perspective view of the bracket/neckband component of FIG. 11.

FIG. 12 shows an underside view of the bracket/neckband component 95 described and depicted in FIG. 11. The assembly 95 may include a tapered extension 96 having a pebble textured underside surface 97 for an enhanced gripping engagement surface with a tube, similar to the tape gripping surface provided by pebble surface 94 depicted in FIG. 11. The underside surface 97 in FIG. 12 may be also slightly contoured 98 to follow the radiused contour of the endotracheal tube. This radiused contour provides a maximum surface engagement with the round outer surface of the tube, such that the tape can form a positive compressive engagement between the bracket extension 96 and the various sized endotracheal tubes.

Figure 13:
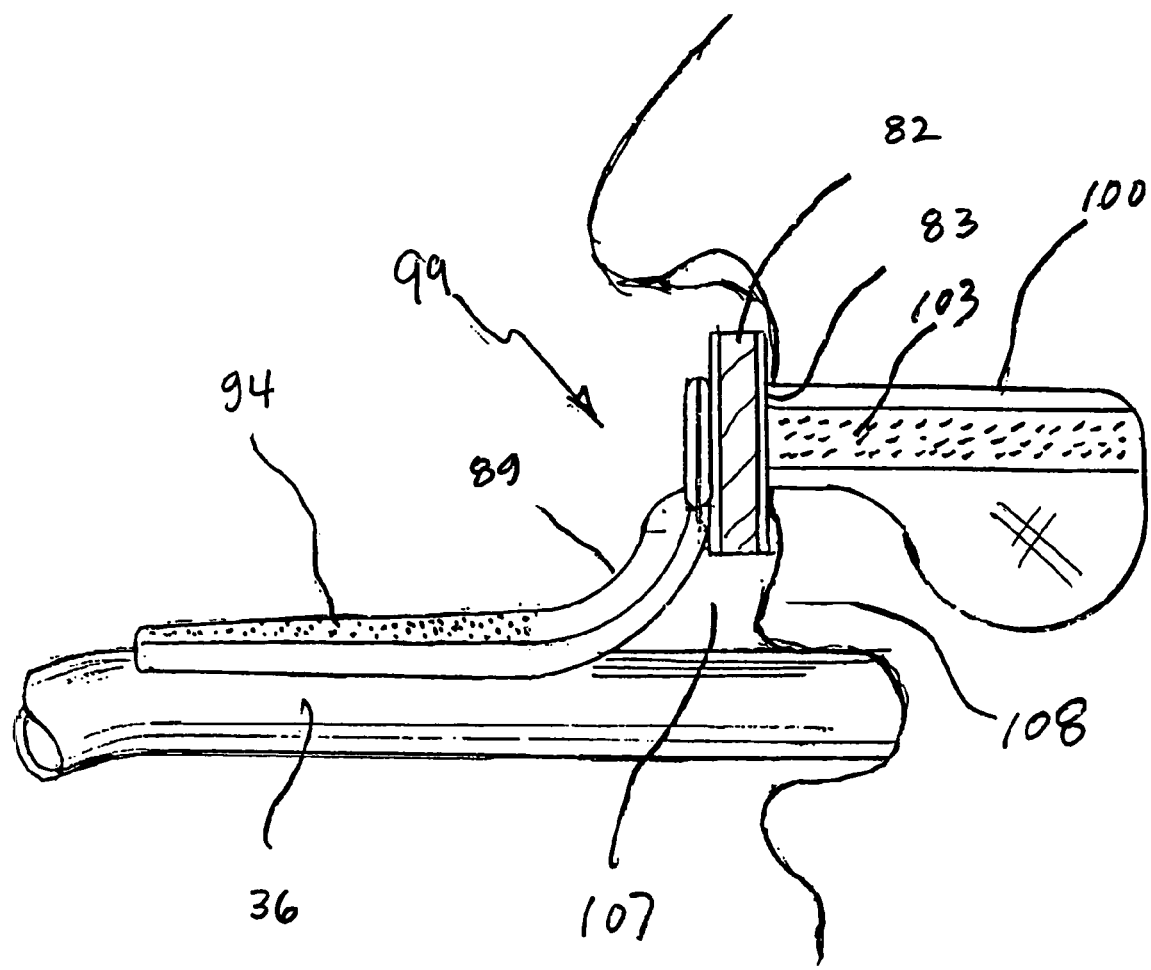
FIG. 13 is a side-view of an assembled endotracheal tube holder assembly of FIG. 11.

FIG. 13 shows a side view of an assembled tube holder assembly 99 comprising a bracket/neckband component 95 of FIGS. 11 and 12 and face anchoring device 100 adhered onto a patient's face region. As with previously described support straps or neckbands, the neckband 82 can include a Velcro™ compatible loop pile material on a back surface 83 which forms a locking mechanical engagement with a Velcro™ hook strip 103 on the face anchoring device 100. Once the bracket extension or arm 94 has been taped onto the endotracheal tube 36, the entire bracket/neckband component 95 functions to keep the tube 36 in a stable, secure position to prevent movement of the tube 36 within the patient's airway. As can be seen, forwardly and curvedly extending bridge portion 89 leaves an air gap or contact-free zone 107 with the patient's upper lip 108. This provides patient comfort in preventing contact with the patient that could otherwise cause pressure sores, skin breakdown, and oral and facial infections, especially in long term intubated patients where the tube holder use may extend to as long as several weeks.

Figure 14:
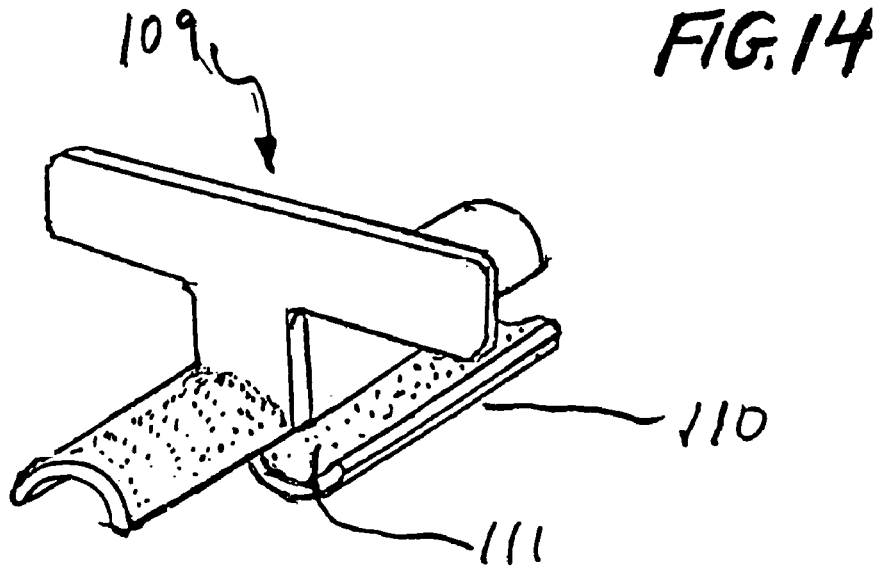
FIG. 14 is a perspective view of an exemplary bracket of a tube holder assembly incorporating a bite block, according to yet another embodiment consistent with the principles of the present invention.
Figure 15:
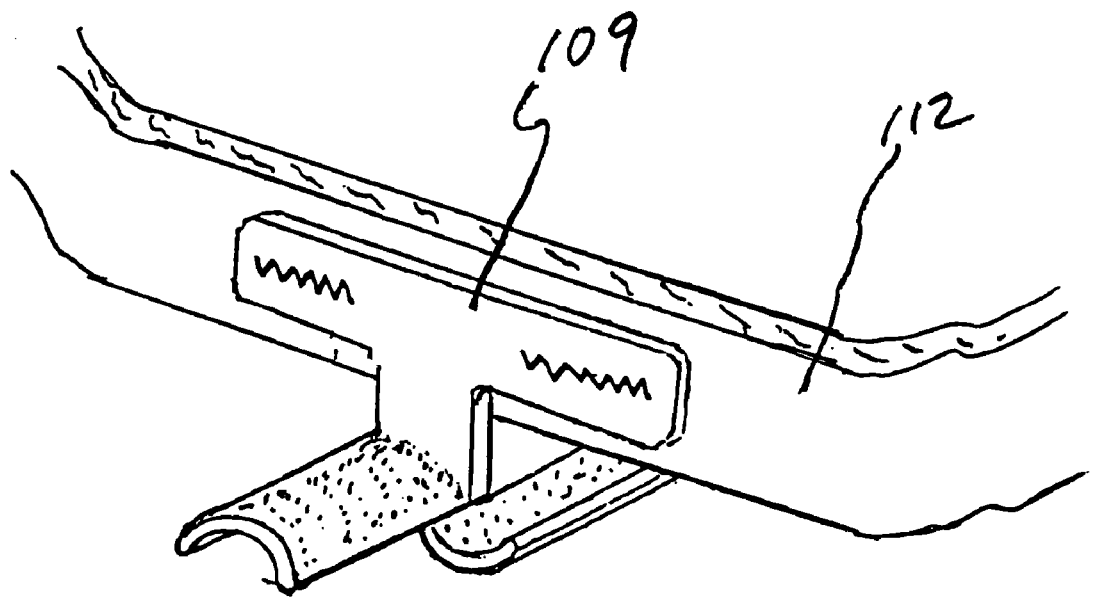
FIG. 15 is a perspective view of the molded one piece bracket with bite block of FIG. 14 attached to a support strap.

FIG. 14 depicts an alternative embodiment of a bracket comprising a one-piece flexible injection molded bracket 109 which incorporates a molded-in rearward bite block 110 including a C-channel for insertion of the endotracheal tube. The C-channel may be configured to form a snap-fitted engagement with the tube. The surface of the bite block 110 may also include surface features, such as for example, surface roughening like a molded-in pebble finish 111 for enhanced engagement to the endotracheal tube. As shown in FIG. 15, the bracket 109 may be stitched onto a neckband 112 similar to those previously described, to form an assembly similar to that depicted in FIG. 11. The C-channel feature can also be applied to other embodiments of the bracket disclosed herein.

Figure 16:
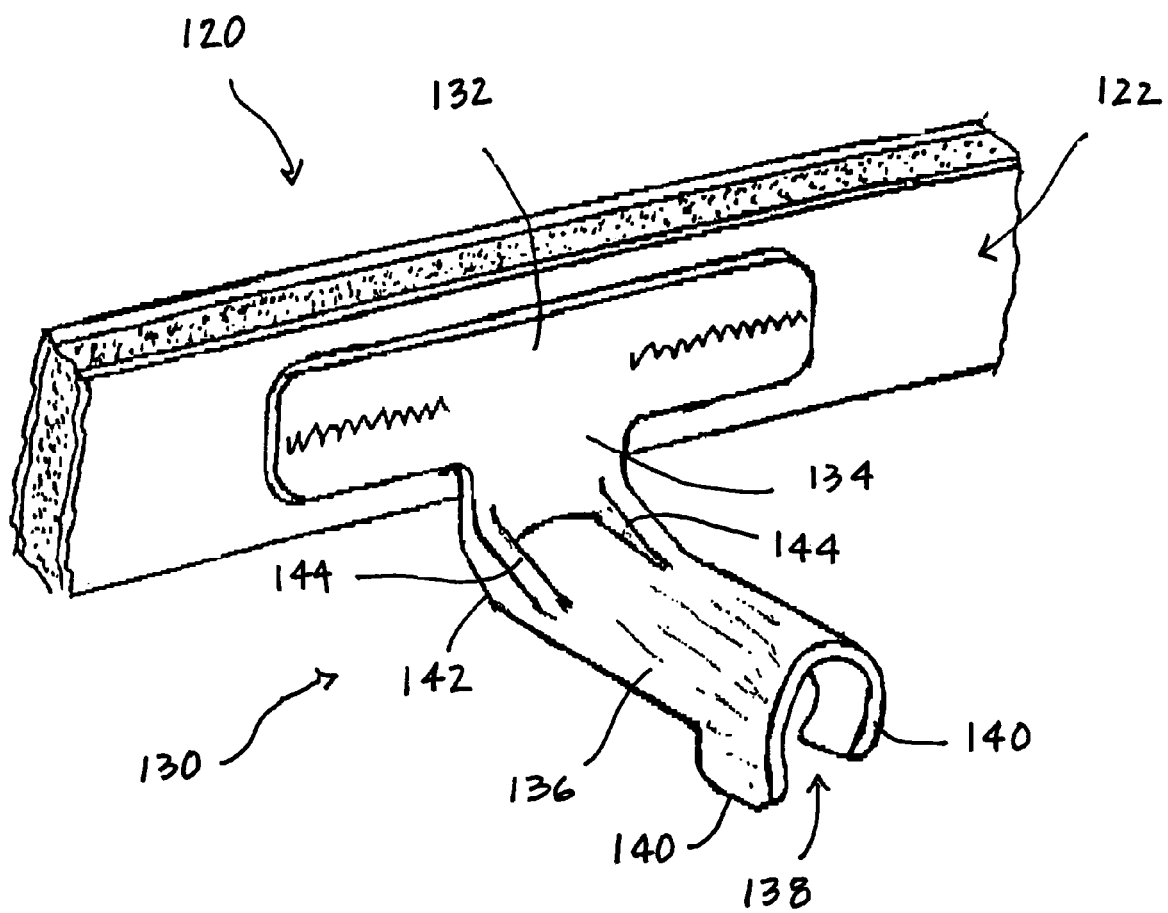
FIG. 16 is a perspective view of a bracket/neckband component of an exemplary endotracheal tube holder assembly, according to even still another embodiment consistent with the principles of the present invention.

FIG. 16 illustrates yet another exemplary embodiment of a bracket/neckband component 120 consistent with the principles of the present invention. As illustrated, the component 120 comprises a neckband 122 similar in all respects to neckband 49 of FIG. 7. A bracket 130 may be affixed to the neckband 122 with stitches, similar to FIG. 7. Further, the bracket 130 may comprise an upper bar 132 from which a bridge portion 134 extends downwardly. The bridge portion 134 extends into a bracket extension or arm 136 that terminates into a gripping region 138 comprising flexible tabs 140 configured for snap-fitting engagement with an endotracheal tube. The bracket extension or arm 134 extends generally perpendicular from the upper bar 132. In order to reduce the pressure point on the patient's lips when assembled, the bracket 130 further includes a contoured junction where the extension or arm 136 meets with the upper bar 132, i.e., the underside of the bridge portion 134 includes chamfered corners 142. This configuration creates an air gap or contact-free zone with the patient's upper lip, improving the patient's comfort and reducing chances for pressure sores, skin breakdown, and oral and facial infections. Reinforcement elements such as molded-in webs or walls 144 may be provided extending between the upper bar 132 and the extension or arm 136, to prevent twisting or torqueing of the bracket 130.

Lastly, a pediatric version of the tube holder assemblies described herein may be provided wherein the sizing of both the neckband and the various styles of bracket is miniaturized and/or dimensionally reduced to fit children between 2 years and up to 12 years old. The bracket/neckband component can therefore be dimensioned to securely hold-pediatric endotracheal tubes from sizes 2 mm up to 6 mm. All this can be done without departing from the teachings of the disclosed invention.

It should be understood that the dimensions and materials described herein are provided merely as a guide to an acceptably sized and constituted tube holder assembly, but can be varied from the measurements and materials specified without departing from the spirit of the invention.

It will be apparent to those skilled in the art that additional various modifications and variations can be made consistent with the present invention without departing from the scope or spirit of the invention. For example, various features within the several embodiments disclosed herein can be combined with features from other tube holder assembly embodiments. Other embodiments consistent with the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A holder assembly for positioning, repositioning, and securing an endotracheal tube in a patient's mouth, the holder assembly comprising:

a neckband having a front surface and an opposed back surface, wherein the back surface includes a first mechanical engagement mating element and is configured for placement above the patient's upper lip, over the patient's cheeks, and around the patient's head or neck region;

a bracket for attachment to the front surface of the neckband for holding the endotracheal tube in position relative to the patient's mouth, the bracket including an upper bar and an arm extending therefrom; and a face anchoring device for securing the neckband to the patient's face region, the face anchoring device comprising a first surface configured to adhere to the patient's face region, and a second, opposed surface having a neckband-engaging portion including a second mechanical engagement mating element capable of mechanical engagement with the first mechanical engagement mating element to enable repeated mechanical engagement and disengagement of the second surface of the face anchoring device with the back surface of the neckband.

2. The holder assembly of claim 1, wherein the bracket is permanently affixed to a fixed position at the front surface of the neckband.

3. The holder assembly of claim 2, wherein the bracket is permanently affixed to the fixed position at the front surface of the neckband by stitching.

4. The holder assembly of claim 1, wherein the first mechanical engagement mating element and the second mechanical engagement mating element form an interlocking relationship.

5. The holder assembly of claim 1, wherein the first mechanical engagement mating element comprises a loop pile material, and the second mechanical engagement mating element comprises a hook material.

6. The holder assembly of claim 1, wherein the arm extends generally perpendicular to the upper bar.

7. The holder assembly of claim 1, wherein the arm terminates in a gripping region configured to form a snap-fitting engagement around the endotracheal tube.

8. The holder assembly of claim 7, wherein the gripping portion comprises tabs configured for gripping the endotracheal tube.

9. The holder assembly of claim 8, wherein the tabs are flexible.

10. The holder assembly of claim 1, wherein the arm further comprises an undercut portion having a generally semi-circular contour.

11. The holder assembly of claim 1, wherein the arm further includes a surface feature for enhanced engagement with the endotracheal tube.

12. The holder assembly of claim 11, wherein the surface feature is selected from the group consisting of surface roughening, barbs, teeth, or adhesive.

13. The holder assembly of claim 1, wherein the upper bar comprises slots for placement of the support strap therethrough.

14. The holder assembly of claim 1, wherein the arm is integral with the upper bar.

15. The holder assembly of claim 1, wherein the junction between the upper bar and arm is contoured.

16. The holder assembly of claim 15, wherein the contoured junction is chamfered.

17. The holder assembly of claim 1, further including reinforcement elements extending between the upper bar and the arm.

18. The holder assembly of claim 1, wherein the neckband comprises releasably attachable closure ends.

19. The holder assembly of claim 18, wherein the closure ends include mechanical engagement surfaces for engaging the front surface of the neckband.

20. The holder assembly of claim 19, wherein the front surface of the neckband comprises a loop pile material and the mechanical engagement surfaces comprise hook material.

21. The holder assembly of claim 1, wherein the first surface of the face anchoring device comprises an adhesive.

22. The holder assembly of claim 1, further including an adhesive tape for securing the endotracheal tube to the arm.

23. The holder assembly of claim 22, wherein the adhesive tape comprises a foam tape.

24. The holder assembly of claim 1, wherein the upper bar comprises a portion of a bite block.

25. The holder assembly of claim 24, wherein the bite block includes a channel for insertion of the endotracheal tube.

26. The holder assembly of claim 25, wherein the channel is configured to form a snap-fitted engagement with the endotracheal tube.

27. A holder assembly for positioning, repositioning, and securing an endotracheal tube to a patient's mouth, the holder assembly comprising:
a neckband having a front surface and an opposed back surface, wherein the back surface includes a first mechanical engagement mating element and is configured for placement above the patient's upper lip, over the patient's cheeks, and around the patient's head or neck region;
a bracket for holding the endotracheal tube in position relative to the patient's mouth, the bracket including an upper bar attached to the front surface of the neckband and an arm extending therefrom, the arm terminating in a gripping region configured to form a snap-fitting engagement around the endotracheal tube; and
a face anchoring device configured to adhere to the patient's face region and mechanically attachable to the back surface of the neckband for securing the neckband to the patient's face region, wherein the face anchoring device comprises a neckband-engaging portion including a second mechanical engagement mating element capable of mechanical engagement with the first mechanical engagement mating element to enable repeated mechanical engagement and disengagement of the back surface of the neckband to the neckband-engaging portion of the face anchoring device.

28. The holder assembly of claim 27, wherein the first mechanical engagement mating element and the second mechanical engagement mating element form an interlocking relationship.

29. The holder assembly of claim 27, wherein the first mechanical engagement mating element comprises a loop pile material, and the second mechanical engagement mating element comprises a hook material.

30. The holder assembly of claim 27, wherein the neckband can be repeatedly released and readjusted to the face anchoring device.

31. The holder assembly of claim 27, wherein the arm extends generally perpendicular to the upper bar.

32. The holder assembly of claim 27, wherein the gripping portion comprises tabs configured for gripping the endotracheal tube.

33. A holder assembly permitting positioning, repositioning and securement of an endotracheal tube in a patient's mouth, the holder assembly comprising:
a neckband having a front surface and an opposed back surface, wherein the back surface includes a first mechanical engagement mating element and is configured for placement above the patient's lip area, over the patient's cheeks, and around the patient's head or neck region;
a bracket for attachment to the front surface of the neckband for holding the endotracheal tube in position relative to the patient's mouth, the bracket including an upper bar and an arm extending therefrom; and a face anchoring device for securing the neckband to the patient's face region, the face anchoring device comprising a first rear surface configured to adhere to the patient's face region, and a second frontal surface having a neckband-engaging portion, said neckband-engaging portion having a second mechanical engagement mating element capable of mechanical engagement with the first mechanical engagement mating element enabling repeated mechanical engagement and disengagement of the neckband-engaging portion with said back surface of said neckband and permitting repositioning of the endotracheal tube along the patient's mouth when the neckband-engaging portion and the back surface are disengaged, and further permitting securement of the neckband to the patient's face region when the neckband-engaging portion and the back surface are engaged capable.

34. A method for positioning, repositioning, and securing an endotracheal tube in a patient's mouth via a holder assembly, wherein the holder assembly comprises a neckband having a front surface and an opposed back surface, the back surface including a first mechanical engagement mating element; and the holder assembly further comprises a bracket attached to the front surface of the neckband and a face anchoring device comprising a first adhesive surface, and an opposed second surface, the second surface having a neckband-engaging portion including a second mechanical engagement mating element capable of mechanical engagement with the first mechanical engagement mating element, the method comprising:

adhering the first adhesive surface of the face anchoring device to a fixed position in the patient's face region;

securing the neckband around the patient's head by placing the back surface of the neckband over the patient's face region, and around the patient's head or neck region;

mechanically engaging a first portion of the first mechanical engagement mating element of the neckband with the neckband-engaging portion of the anchoring device at the fixed position;

attaching the endotracheal tube to the bracket in a first position relative to the patient's mouth; and repositioning the endotracheal tube to a second position relative to the patient's mouth different from the first position, wherein the repositioning comprises:

mechanically disengaging the first portion from the neckband-engaging portion, moving the neckband such that a second portion of the first mechanical engagement mating element of the neckband, different from the first portion, contacts the neckband-engaging portion of the anchoring device at the fixed position and such that the endotracheal tube is positioned at the second position relative to the patient's mouth, and mechanically engaging the second portion with the neckband engaging portion of the anchoring device at the fixed position.

35. A holder assembly for positioning an endotracheal tube in a patient's mouth, the holder assembly comprising:

a neckband having a front surface and an opposed back surface, wherein the back surface includes a first mechanical engagement mating element;

a bracket for attachment to the front surface of the neckband for holding the endotracheal tube in position relative to the patient's mouth; and a face anchoring device for securing the neckband to the patient's face region, the face anchoring device comprising a first surface configured to adhere to the patient's face region, and a second, opposed surface having a neckband-engaging portion including a second mechanical engagement mating element capable of mechanical engagement with the first mechanical engagement mating element to enable repeated mechanical engagement and disengagement of the face anchoring device with the back surface of the neckband.

36. The holder assembly of claim 35, wherein the first mechanical engagement mating element and the second mechanical engagement mating element form an interlocking relationship.

37. The holder assembly of claim 35, wherein the first mechanical engagement mating element comprises a loop pile material, and the second mechanical engagement mating element comprises a hook material.

38. The holder assembly of claim 35, wherein the first mechanical engagement mating element comprises a hook material, and the second mechanical engagement mating element comprises a loop pile material.

* * * * *